United States Patent
Conrad (10) Patent No.: US 9,216,086 B2
(45) Date of Patent: Dec. 22, 2015

(54) ADJUSTABLE PROVISIONAL COMPONENT OF A MEDICAL DEVICE

(71) Applicant: Paul J. Conrad, West Chester, OH (US)

(72) Inventor: Paul J. Conrad, West Chester, OH (US)

(73) Assignee: Zimmer, Inc., Warsaw, IN (US)

( * ) Notice: Subject to any disclaimer, the term of this patent is extended or adjusted under 35 U.S.C. 154(b) by 380 days.

(21) Appl. No.: 13/746,618

(22) Filed: Jan. 22, 2013

(65) Prior Publication Data

US 2013/0197656 A1 Aug. 1, 2013

Related U.S. Application Data

(60) Provisional application No. 61/593,494, filed on Feb. 1, 2012.

(51) Int. Cl.
| | |
|---|---|
| *A61F 2/32* | (2006.01) |
| *A61F 2/46* | (2006.01) |
| A61F 2/36 | (2006.01) |
| A61F 2/38 | (2006.01) |
| A61F 2/40 | (2006.01) |
| A61F 2/30 | (2006.01) |

(52) U.S. Cl.
CPC ........... *A61F 2/32* (2013.01); *A61F 2/4684* (2013.01); *A61F 2/3609* (2013.01); *A61F 2/38* (2013.01); *A61F 2/4014* (2013.01); *A61F 2002/3055* (2013.01); *A61F 2002/469* (2013.01); *A61F 2002/4658* (2013.01); *A61F 2002/4668* (2013.01)

(58) Field of Classification Search
CPC ......... A61F 2/468; A61F 2/4684; A61F 2/32; A61F 2/38; A61F 2/3609
USPC ............... 623/23.45, 23.47, 57, 22.11, 23.39, 623/23.15, 23.11, 22.42, 22.4
See application file for complete search history.

(56) References Cited

U.S. PATENT DOCUMENTS

| | | | | |
|---|---|---|---|---|
| 5,176,683 | A * | 1/1993 | Kimsey et al. | 606/86 R |
| 5,336,268 | A * | 8/1994 | Rispeter | 623/22.4 |
| 5,350,379 | A * | 9/1994 | Spievack | 606/63 |
| 5,387,239 | A * | 2/1995 | Bianco et al. | 623/23.45 |
| 5,415,660 | A * | 5/1995 | Campbell et al. | 606/62 |
| 5,569,263 | A * | 10/1996 | Hein | 606/102 |
| 5,704,938 | A * | 1/1998 | Staehlin et al. | 606/62 |
| 5,733,292 | A * | 3/1998 | Gustilo et al. | 606/88 |
| 5,800,554 | A * | 9/1998 | Scholz | 623/22.43 |
| 5,888,211 | A * | 3/1999 | Sanders | 623/22.4 |
| 6,083,263 | A * | 7/2000 | Draenert et al. | 623/22.46 |
| 6,245,109 | B1 * | 6/2001 | Mendes et al. | 623/18.11 |
| 6,336,929 | B1 * | 1/2002 | Justin | 606/63 |
| 6,447,448 | B1 * | 9/2002 | Ishikawa et al. | 600/300 |
| 6,530,957 | B1 * | 3/2003 | Jack | 623/19.14 |
| 6,569,203 | B1 * | 5/2003 | Keller | 623/23.47 |
| 6,723,102 | B2 * | 4/2004 | Johnson et al. | 606/79 |
| 6,974,483 | B2 * | 12/2005 | Murray | 623/22.42 |
| 7,097,663 | B1 * | 8/2006 | Nicol et al. | 623/19.13 |
| 7,125,423 | B2 * | 10/2006 | Hazebrouck | 623/16.11 |
| 7,135,022 | B2 * | 11/2006 | Kosashvili et al. | 606/63 |

(Continued)

*Primary Examiner* — Alvin Stewart
(74) *Attorney, Agent, or Firm* — Schwegman Lundberg & Woessner, P.A.

(57) ABSTRACT

An adjustable provisional component for an implantable medical device comprises a first portion mountable to a first part of a patient, and a second portion coupled to the first portion, wherein at least one of the first portion and the second portion is adjustable to select a value of a first geometric parameter of the adjustable provisional component.

18 Claims, 4 Drawing Sheets

(56) References Cited

U.S. PATENT DOCUMENTS

| | | | |
|---|---|---|---|
| 7,338,499 B1* | 3/2008 | Kuczynski et al. | 606/102 |
| 7,425,214 B1* | 9/2008 | McCarthy et al. | 606/89 |
| 7,559,951 B2* | 7/2009 | DiSilvestro et al. | 623/23.47 |
| 7,604,637 B2* | 10/2009 | Johnson et al. | 606/81 |
| 7,608,112 B1* | 10/2009 | Kuczynski et al. | 623/22.11 |
| 7,753,915 B1* | 7/2010 | Eksler et al. | 606/105 |
| 8,052,758 B1* | 11/2011 | Winslow | 623/22.42 |
| 8,252,063 B2* | 8/2012 | Stauch | 623/23.47 |
| 8,419,801 B2* | 4/2013 | DiSilvestro et al. | 623/23.47 |
| 8,428,693 B2* | 4/2013 | Meulink | 600/427 |
| 8,623,092 B2* | 1/2014 | Bickley et al. | 623/18.11 |
| 8,778,029 B2* | 7/2014 | Baumgart | 623/22.4 |
| 2001/0007957 A1* | 7/2001 | Martin et al. | 623/23.17 |
| 2002/0120339 A1* | 8/2002 | Callaway et al. | 623/19.14 |
| 2002/0151978 A1* | 10/2002 | Zacouto et al. | 623/17.12 |
| 2002/0193797 A1* | 12/2002 | Johnson et al. | 606/79 |
| 2003/0018393 A1* | 1/2003 | Skiera | 623/35 |
| 2003/0032958 A1* | 2/2003 | Soubeiran | 606/61 |
| 2003/0153978 A1* | 8/2003 | Whiteside | 623/20.21 |
| 2004/0030395 A1* | 2/2004 | Blunn et al. | 623/18.12 |
| 2004/0243148 A1* | 12/2004 | Wasielewski | 606/130 |
| 2005/0060030 A1* | 3/2005 | Lashinski et al. | 623/2.37 |
| 2005/0071014 A1* | 3/2005 | Barnett et al. | 623/19.14 |
| 2005/0246034 A1* | 11/2005 | Soubeiran | 623/23.45 |
| 2005/0261779 A1* | 11/2005 | Meyer | 623/23.47 |
| 2005/0288681 A1* | 12/2005 | Klotz et al. | 606/102 |
| 2006/0004459 A1* | 1/2006 | Hazebrouck et al. | 623/18.12 |
| 2006/0111790 A1* | 5/2006 | Dietz | 623/20.32 |
| 2006/0142866 A1* | 6/2006 | Baratz et al. | 623/20.11 |
| 2007/0078519 A1* | 4/2007 | Klotz | 623/23.47 |
| 2007/0233267 A1* | 10/2007 | Amirouche et al. | 623/20.14 |
| 2007/0234819 A1* | 10/2007 | Amirouche et al. | 73/781 |
| 2010/0168867 A1* | 7/2010 | Swain et al. | 623/23.49 |
| 2010/0198351 A1* | 8/2010 | Meulink | 623/16.11 |
| 2011/0196435 A1* | 8/2011 | Forsell | 606/86 R |
| 2012/0209269 A1* | 8/2012 | Pool et al. | 606/63 |
| 2012/0216611 A1* | 8/2012 | Stein et al. | 73/379.01 |
| 2013/0079678 A1* | 3/2013 | Stein et al. | 600/594 |
| 2013/0079888 A1* | 3/2013 | Meulink | 623/22.42 |
| 2013/0103160 A1* | 4/2013 | Young | 623/20.32 |
| 2013/0116797 A1* | 5/2013 | Coulange et al. | 623/21.18 |
| 2013/0197656 A1* | 8/2013 | Conrad | 623/22.11 |
| 2013/0261759 A1* | 10/2013 | Claypool et al. | 623/20.33 |
| 2013/0267959 A1* | 10/2013 | Engh et al. | 606/90 |
| 2013/0289739 A1* | 10/2013 | Anapliotis et al. | 623/23.45 |
| 2014/0371865 A1* | 12/2014 | Jordan et al. | 623/20.32 |

* cited by examiner

ADJUSTABLE PROVISIONAL COMPONENT OF A MEDICAL DEVICE

CLAIM OF PRIORITY

This application claims the benefit of priority under 35 U.S.C. §119(e) of Conrad, U.S. Provisional Patent Application Ser. No. 61/593,494, entitled "ADJUSTABLE PROVISIONAL COMPONENT OF A MEDICAL DEVICE", filed on Feb. 1, 2012, which is herein incorporated by reference in its entirety.

BACKGROUND

During some orthopedic surgeries a surgeon or other medical practitioner can use a provisional component to test a particular orthopedic-implant geometry. For example, during total hip arthroplasty (THA) or total hip replacement (THR) surgery, a stem is implanted into the femur of the patient and the surgeon or other medical practitioner fits one or more provisional femoral heads to the stem in order to determine geometric parameters that provide an acceptable fit with the patient's anatomy. Each provisional head can provide for a particular leg length, a particular lateral offset between the center of the femoral head and the center of the femur, and a particular version angle. A tray of provisional heads can be provided to the surgeon or other medical practitioner by an orthopedic device company, with each provisional head corresponding to a model of permanent head.

After fitting a provisional head to the stem, the surgeon or other medical practitioner can test the hip geometry of the provisional head and the patient's range of motion to determine if the geometry of the provisional head provides for a desirable fit. If the surgeon or other medical practitioner is unsatisfied with the geometry of the first provisional head, for example, the surgeon or other medical practitioner can select a second provisional head from the tray and fit the second provisional next to the stem and repeat testing the patient's hip geometry and range of motion. This process is repeated until an acceptable fit is achieved.

SUMMARY

The present disclosure relates generally to an adjustable provisional component for an implantable medical device that provides for the implantation of a provisional component into the patient, followed by in vivo adjustment of geometric parameters of the component so that a surgeon or other medical practitioner can quickly and easily determine a proper geometry of a final permanent implant. For example, an adjustable provisional femoral head component can be used during total hip arthroplasty (THA) or total hip replacement (THR) surgery, wherein parameters such as leg length and lateral offset can be adjusted in vivo, such as with a robotic control mechanism.

In an example, an adjustable provisional component for an implantable medical device is provided. The example adjustable provisional component comprises a first portion mountable to a first part of a patient, and a second portion coupled to the first portion, wherein at least one of the first portion and the second portion is adjustable to select a value of a first geometric parameter of the adjustable provisional component.

In an example, a system comprises an adjustable provisional component comprising a first portion mountable to a first part of a patient, and a second portion coupled to the first portion, wherein at least one of the first portion and the second portion is adjustable to select a value of a first geometric parameter of the adjustable provisional component, a control mechanism for adjusting the at least one of the first portion and the second portion to adjust the first geometric parameter, and a controlling computer configured to control the control mechanism.

In an example, an adjustable orthopedic provisional component comprises an adjustable neck mountable to a stem of an artificial hip implant, a head mountable to the adjustable neck, wherein the neck is adjustable to select a value of one of a leg length adjustment, a value of a lateral offset between the head and the stem, or a version angle, and a control mechanism for adjusting the neck to adjust the one of the leg length adjustment, the lateral offset between the head and the stem, or the version angle.

This summary is intended to provide an overview of subject matter of the present disclosure. It is not intended to provide an exclusive or exhaustive explanation of the invention. The detailed description is included to provide further information about the present disclosure.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present disclosure relates generally to an adjustable provisional component for a medical device, such as an adjustable provisional orthopedic component, that can be temporarily implanted within a patient, followed by in vivo adjustment of geometric parameters of the component so that a surgeon or other medical practitioner can quickly and easily determine a proper geometry of a final permanent implant. For example, an adjustable provisional femoral head component can be used during total hip arthroplasty (THA) or total hip replacement (THR) surgery, wherein geometric parameters such as leg length, lateral offset, and version angle can be adjusted in vivo, such as with a robotic control mechanism. The adjustable provisional component can be controlled by a controlling device, such as a computer operated by the surgeon or other medical practitioner, that automatically adjusts the geometry of the adjustable provisional component so that selected values of one or more geometric parameters are achieved.

Figure 1:
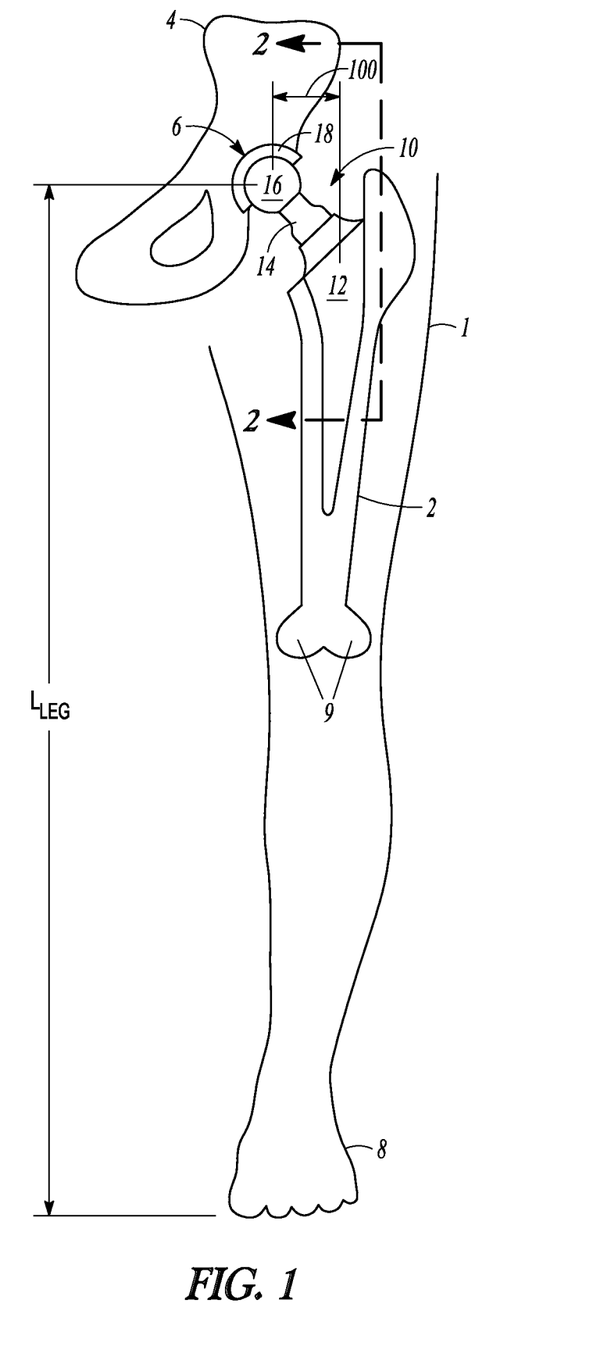
FIG. 1 is a conceptual front view of an example implantable medical device comprising an example artificial hip implant showing examples of geometric parameters of interest for the artificial hip implant.

FIG. 1 shows a conceptual view of a permanent artificial hip implant 10 implanted within a patient 1. In an example, hip implant 10 comprises a stem 12, a neck 14, and a head 16. Stem 12 can be implanted within the femur 2 of patient 1, such as by being inserted and affixed (e.g., naturally or in conjunction with an adhesive, such as bone cement) into the medullary canal of femur 2. Neck 14 can be integrally formed with or coupled to stem 12, and head 16 can be coupled to or otherwise associated with neck 14. Head 16 engages the acetabulum 6 of the patient's pelvis 4. In some examples, a liner 18 can be affixed in acetabulum 6 so that head 16 will smoothly slide within acetabulum 6. In still further embodiments, the acetabulum can be prepared to receive an acetabular cup, such as the Allofit®, Trilogy® or Continuum® cup available from Zimmer, Inc. (Warsaw, Ind.).

Figure 2:
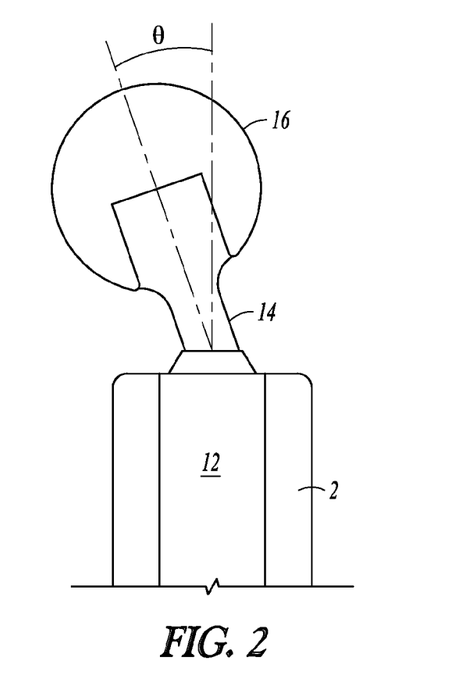
FIG. 2 is a conceptual side view of the example artificial hip implant of FIG. 1.

The geometry of stem 12, neck 14, and head 16 provides for specific geometric parameters that are typically used by medical practitioners, such as orthopedic surgeons, to define the fit and geometry of a patient's hip joint. One geometric parameter that can be of interest is the leg length $L_{Leg}$, which can be described as the length from the center of head 16 to the bottom of the patients foot 8. Another geometric parameter that can be of interest is the "lateral offset" or simply "offset" 100 which can be described as the distance between a center of head 16 and a central longitudinal axis of stem 12. Another geometric parameter that can be of interest is the version angle $\theta$, shown in FIG. 2, which can be described as the angle between a lateral axis of femur 2, wherein the lateral axis is generally defined by the distal condyls 9 of femur 2, and a central longitudinal axis of neck 14 when viewed laterally, as in FIG. 2. For some patients, the natural version angle $\theta$ directs neck 14, when running from femur 2 and stem 12 to head 16, toward the patient's anterior, as shown in FIG. 2, also referred to as femoral anteversion. For other patients, the natural version angle can direct neck 14, when running from femur 2 and stem 12 to head 16, toward the patient's posterior, also referred to as femoral retroversion.

The geometric parameters that can be adjusted by adjustable provisional component 20 are not limited to leg length adjustment, lateral offset, and version angle, nor is adjustable provisional component 20 limited to a provisional hip component. Rather, medical devices other than artificial hip implants, such as other types of orthopedic implants or types of medical devices other than orthopedic devices, can have other geometric parameters that can be of interest. The particular geometric parameters that may be adjusted by adjustable provisional component 20 can depend on the type of medical device, the portion of the patient that the medical device acts upon, the specific procedure for which the adjustable provisional component 20 is being used, and standard medical practices for the type of medical device or procedure, among other reasons.

During hip replacement surgery, such as total hip replacement (THR) surgery, also referred to as total hip arthroplasty (THA) surgery, a temporary neck and head can be fitted onto stem 12 implanted into the patient's femur 2. The temporary neck and head are only used during the surgery to ensure that an artificial hip with an appropriate geometry for the patient is used. This type of temporary neck and head can be referred to herein as a "provisional neck" and a "provisional head," in order to distinguish the provisional neck and head from the neck and head of a permanent implant. During surgery, the surgeon or other medical practitioner fits a provisional neck and provisional head onto stem 12, where the provisional neck has a geometry that is substantially the same as the geometry of a permanent neck 14 and the provisional head has a geometry that is substantially the same as the geometry of a permanent head 16. The surgeon or other medical practitioner can then test the hip geometry of the provisional neck and provisional head and its compatibility with the patient's hip anatomy, such as by testing the patient's range of motion and the physical interaction between the provisional component with the patient, e.g., with the patient's femur 2, pelvis 4, acetabulum 6, etc. This testing process is sometimes referred to as a partial hip reduction.

A tray including a plurality of provisional necks and provisional heads of various geometries can be provided to the surgeon or other medical practitioner. For example, the tray can be configured with certain number of provisional necks, e.g., as many as 20 or more provisional necks, wherein each provisional neck can provide for a corresponding leg length adjustment, a corresponding lateral offset, and a corresponding version angle. If the first provisional neck selected by the surgeon or other medical practitioner does not provide for an acceptable hip geometry and range of motion, the surgeon or other medical practitioner removes the provisional neck or head from the patient and fits another provisional neck or head onto the stem and once again performs a partial hip reduction to determine if the second provisional neck or head provides for acceptable hip geometry and range of motion. This process can be repeated by the surgeon or other medical practitioner until a desirable fit is achieved. A permanent hip implant with a geometry corresponding to that of the provisional neck and provisional head are then implanted into the patient. It is not uncommon for a surgeon or other medical practitioner to use four or more different provisional necks before finding the geometry that was appropriate for the patient.

Figure 3:
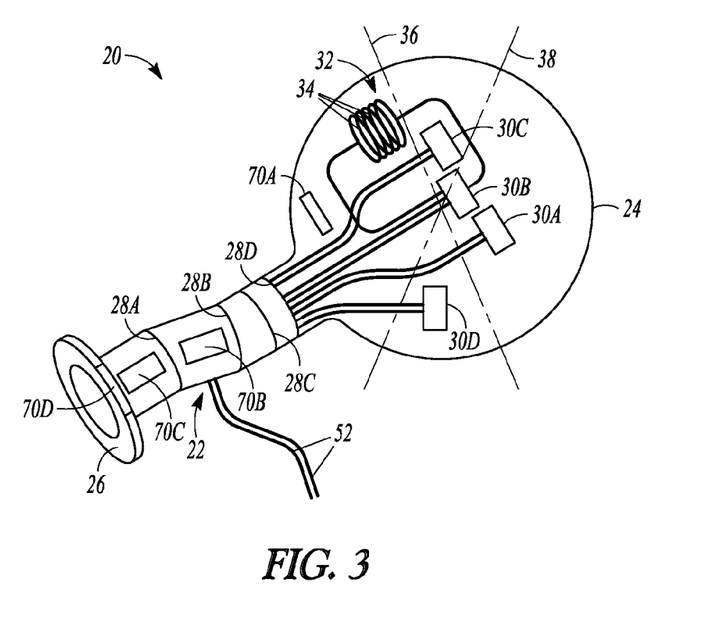
FIG. 3 is a perspective view of an example adjustable provisional component that allows for adjustment of one or more geometric parameters of interest.

FIG. 3 shows an example of an adjustable provisional component 20 that can provide for a plurality of values of one or more geometric parameters that are relevant to the operation of the implanted provisional component. In the example of FIG. 3, adjustable provisional component 20 comprises a provisional neck and provisional head for an artificial hip implant. As noted above, the adjustable provisional component 20 of the present disclosure is not limited to an artificial hip implant, but could be used for any type of medical device where a provisional component can be used during surgery to determine a parameter, such as a geometric parameter, that will be adequate for a particular patient, such as other orthopedic provisional components or components of other types of medical devices. For example, an adjustable provisional component similar to component 20 shown in FIG. 3 could be provided for an artificial shoulder implant, an artificial elbow implant, an artificial knee implant, an artificial ankle implant, or any other medical device where a provisional component can be used. For the sake of brevity, adjustable provisional component 20 will be described as a provisional component for an artificial hip.

The example adjustable provisional hip component 20 shown in FIG. 3 comprises a provisional neck 22 and a provisional head 24. A connector 26 can provide for a connection between provisional neck 22 and a stem implanted within femur 2, such as stem 12 shown in FIG. 1. In an example, adjustable provisional hip component 20 comprises one or more adjustable structures that allow for adjustment of at least one geometric parameter. In an example, the at least one adjustable structure can comprise one or more joints 28A, 28B, 28C, and 28D (referred to collectively herein as "joint 28" or "joints 28") within provisional neck 22. Joints 28 can allow at least one geometric parameter of provisional component 20 to be adjusted. For example, joints 28 can be adjusted so that the overall offset between a center of provisional head 24 and a center of the stem connected to connector 26 can be changed, e.g., from a small offset of about 30 millimeters to a large offset of about 60 millimeters. The adjustable structure can also comprise a structure or mechanism for adjusting the axial length of provisional hip component 20 in order to provide control over the patient's overall leg length, such as with a piston where the length of the piston can be selected. Joints 28 can also be adjusted to control version angle θ.

In an example, provisional component 20 also includes one or more control mechanisms 30A, 30B, 30C, and 30D (referred to collectively herein as "control mechanism 30" or "control mechanisms 30") for adjusting one or more geometric parameters of provisional component 20, such as patient leg length, lateral offset, or version angle for an artificial hip component 20. In an example, each control mechanism 30 comprises a mechanical mechanism capable of physically moving component 20 in order to change one or more geometric parameters, such as a servo motor or a jack screw. In the example shown in FIG. 3, control mechanisms 30 are located within provisional head 24. A power supply 32, such as one or more batteries 34, can also be housed within provisional head 24.

In an example, provisional component 20 comprises at least three control mechanisms 30, such as a first control mechanism 30A (e.g., a first jack screw 30A), a second control mechanism 30B (e.g., second jack screw 30B), and a third control mechanism 30C (e.g., third jack screw 30B). First control mechanism 30A and second control mechanism 30B can control the relative alignment of provisional head 24 with respect to provisional neck 22, such as first control mechanism 30A controlling a tilt of provisional head 24 with respect to provisional neck 22 generally along a first axis 36 and second control mechanism 30B controlling a tilt of provisional head 24 with respect to provisional neck 22 generally along a second axis 38, wherein first axis 36 can be generally orthogonal to second axis 38. Together, first control mechanism 30A and second control mechanism 30B can tilt provisional head 24 in any orientation with respect to provisional neck 22, which can, in turn, provide for control of the lateral offset and the version angle θ of adjustable provisional hip component 20.

A third control mechanism 30C can be configured to alter the leg length of patient 1, e.g., by altering the total length of provisional neck 22. In an example, a fourth control mechanism 30D (e.g., fourth jack screw 30D) can be included to adjust an angle formed by one or more of joints 28, e.g., joint 28A, 28B, or 28C. A person of ordinary skill can readily determine a setting for each control mechanism 30 in order to provide for a desired value of one or more geometric parameters, such as patient leg length, later offset, and version angle θ.

Figure 4:
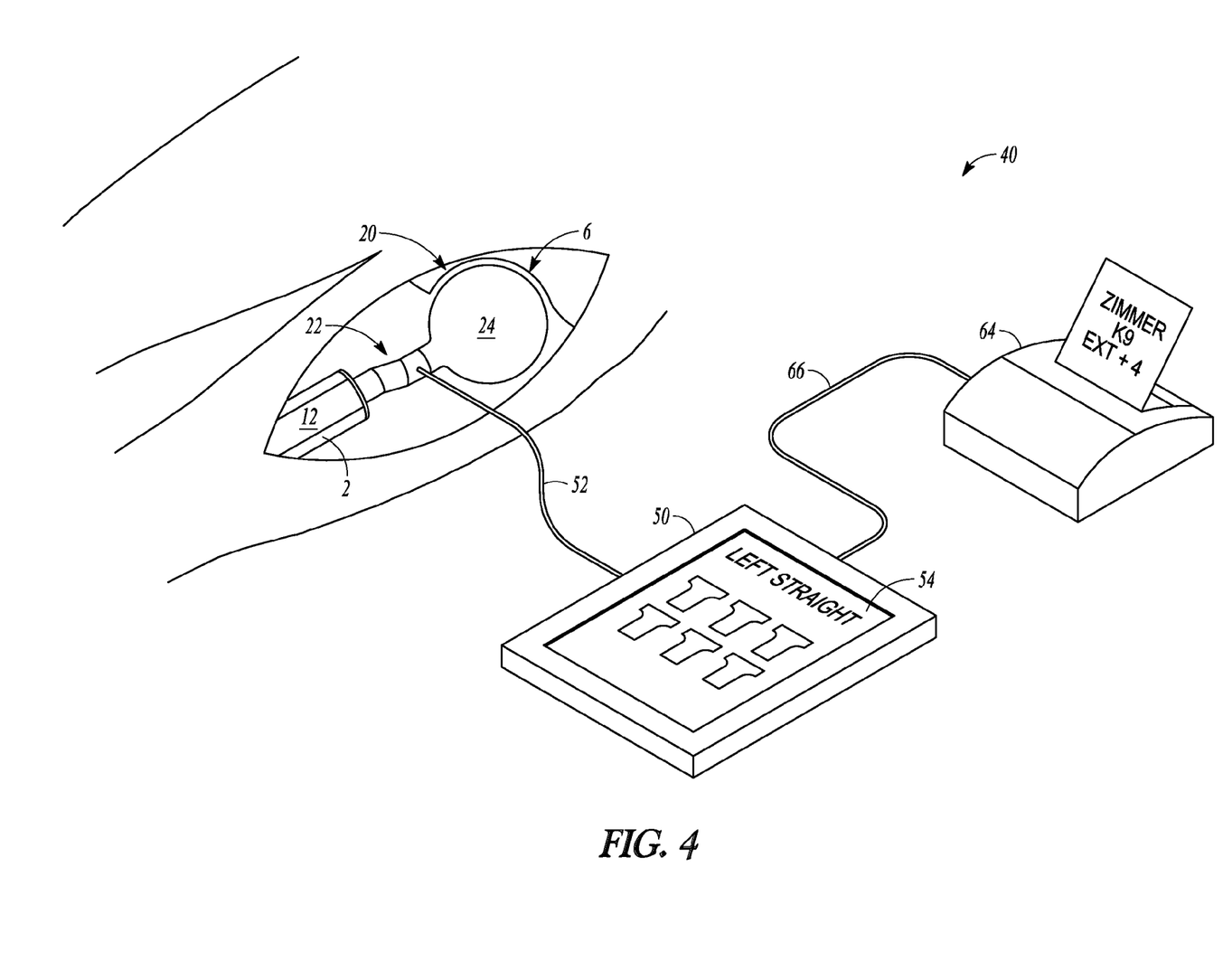
FIG. 4 is a conceptual view of a system comprising the example adjustable provisional component of FIG. 3 and an example user control device configured to control the adjustable provisional component.

FIG. 4 shows a diagram of an example system 40 comprising an adjustable provisional component 20 and a controller 50 for communicating with and controlling adjustable provisional component 20. Controller 50 is configured to control the one or more control mechanisms 30 in order to adjust one or more geometric parameters of provisional component 20. Controller 50 provides a means for a user, such as a surgeon or other medical practitioner performing an orthopedic surgery, to select a specific value of one or more geometric parameters of interest for provisional component 20. After the specific geometry is selected, controller 50 causes control mechanisms 30 to adjust the one or more geometric parameters in order to achieve the selected geometry. For example, for the example provisional hip component 20 shown in FIG. 3, a surgeon or other user can input a specific leg length, lateral offset, and version angle at controller 50, and controller 50 can direct control mechanisms 30 to move such that the selected leg length adjustment, lateral offset, and version angle are achieved.

Figure 5:
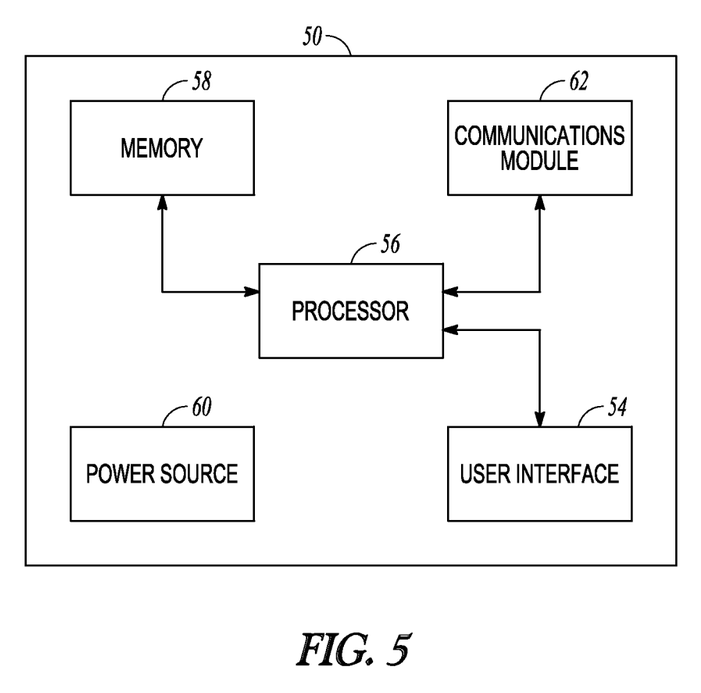
FIG. 5 is a schematic diagram of an example user controller device configured to control one or more control mechanisms of the example adjustable provisional component.

In an example, controller 50 comprises a computing device that is communicatively coupled to adjustable provisional component 20, such as via one or more wires 52 or a wireless communication link (not shown). FIG. 5 is a schematic diagram of an example controller 50 comprising a user interface 54 to provide a user with control over controller 50, a processor 56 for controlling the components of controller 50, a memory 58 for storing instructions or other parameters that can be used by processor 56, a power source 60, such as a battery or a connection to alternating current power, and a communication module 62 that communicates with the one or more control mechanisms 30 to relay instructions from processor 56 to control mechanisms 30 of adjustable provisional component 20.

User interface 54 presents a user, such as a surgeon or other medical practitioner, with information about adjustable provisional component 20 and allows the user to select values of one or more geometric parameters of adjustable provisional component 20 in order to determine the best geometric fit for the patient. In an example, shown in FIG. 4, user interface 54 comprises a touch screen. As described in more detail below, the visual layout of a touch screen user interface 54 can be configured to visually resemble a physical provisional neck tray that can have been previously used by the surgeon or other medical practitioner in order to avoid confusion or to aid adoption by the medical practitioner. The user interface can also comprise any other interface that will allow the user to input or select values of geometric parameters. Examples of user interfaces include, but are not limited to, a touch screen, such as a capacitive touch screen, a resistive touch screen, a surface acoustic wave, an infrared touch screen, an optical imaging touch screen, a dispersive signal or piezoelectric touch screen, or an acoustic pulse recognition touch screen, a monitor and an input device, such as a keyboard or pointing device such as a stylus or a mouse.

Processor 56 can be included in controller 50 in order to direct the one or more control mechanisms 30, e.g., by managing control signals sent to control mechanisms 30 in order to control the position of control mechanisms 30 and thus control values of geometric parameters of interest. Processor 56 can execute instructions stored on memory 58. Processor 56 can comprise a microprocessor, a controller, a digital signal processor (DSP), an application specific integrated circuit (ASIC), a field-programmable gate array (FPGA), or any other equivalent integrated or discrete logic circuitry, as well as combinations of such components. Memory 58 can include any volatile, non-volatile, magnetic, optical, or electrical storage medium, such as a random access memory (RAM), read-only memory (ROM), non-volatile RAM (NVRAM), magnetic RAM (MRAM), electrically-erasable programmable ROM (EEPROM), flash memory, and the like.

In an example, a plurality of sets of predetermined output values or control signal values for control mechanisms 30 can be stored in memory 58. Each output value can comprise a particular output of a particular control mechanism 30, e.g., a particular position of a jack screw or servo motor. Each control signal value can comprise a value of a control signal that is transmitted to one or more control mechanism 30 to achieve a particular output. Each set of predetermined values can comprise output values or control signals that can provide for a particular value or set of values of one or more geometric parameters that can be adjusted by adjustable provisional component 20. For example, for the adjustable provisional hip component 20 described above with respect to FIG. 3, a first set of control mechanism output values or control signal values can be stored on memory 58 that provides for a first output value or control signal value for first control mechanism 30A, a first output value or control signal value for second control mechanism 30B, a first output value or control signal value for third control mechanism 30C, and a first output value or control signal value for fourth control mechanism 30D (if present), wherein the output values or control signal values for control mechanisms 30A-30D provide for a first leg length adjustment, a first lateral offset, and a first version angle. Similarly, a second set of control mechanism output values can also be stored on memory 58 that provide for a second output value or control signal value for first control mechanism 30A, a second output value or control signal value for second control mechanism 30B, a second output value or control signal value for third control mechanism 30C, and a second output value or control signal value for fourth control mechanism 30D (if present) providing for a second leg length adjustment, a second lateral offset, and a second version angle. Further sets of control signal values or control signal values (e.g., a third set, a fourth set, a fifth set, and so on) can be stored on memory 58 for each combination of geometric parameter values that adjustable provisional component 20 can take.

Sets of control mechanism output values or control signal values can be stored on memory 58 to provide for nearly limitless combinations of each geometric parameter. For example, continuing with the example of an adjustable provisional hip component 20, sets of control mechanism output values or control signal values can be stored in memory 58 to provide for any combination of a predetermined set of leg length adjustment values, a predetermined set of lateral offset values, and a predetermined set of version angle values. The values of each geometric parameter that can be adjusted can correspond to the values that are available for a permanent implant that can be implanted in patient 1.

As an example, for total hip replacement surgery, an example set of artificial hip implants that can be provided for patient 1 is the M/L TAPER HIP PROSTHESIS line of artificial hip implants sold by Zimmer, Inc. (Warsaw, Ind.). The M/L TAPER HIP PROSTHESIS line provides artificial hips having leg length values of −8, −4, +0, +4, and +8 (with each value being defined as the number of millimeters from a "base" configuration). The M/L TAPER HIP PROSTHESIS line also provides lateral offset parameters of "Extra Reduced," "Reduced," "Standard," "Extended," and "Extra Extended." Finally, the M/L TAPER HIP PROSTHESIS line can be selected to have a version angle that is anteverted, straight, or retroverted. In order to accommodate each possible combination, a set of control mechanism output values or control signal values for each combination (e.g., a first set for −8 leg length, Extra Reduced offset, and anteverted, a second set for −4 leg length, Extra Reduced offset, and anteverted, and so on) so that a user, such as a surgeon or other medical practitioner, can select a particular leg length, a particular lateral offset, and a particular version angle, and processor 56 can automatically select the proper set of control mechanism output values or control signal values from memory 58.

One approach for using provisional components includes the use of a tray of provisional components, e.g., a tray of provisional necks and heads for a hip implant that can be provided to a surgeon or other medical practitioner for use during a surgery. In an example, the tray of provisional components can be provided to the surgeon or other medical practitioner in a two-dimensional array with a first geometric parameter changing along a first axis (e.g., the X axis) of the tray, and a second geometric parameter changing along a second axis (e.g., the Y axis) of the tray. In an example of a tray for a provisional hip implant, a provisional tray comprises an array of five (5) rows and five (5) columns of provisional necks. When moving along a particular row, e.g., from left to right along the tray, a first geometric parameter, such as a lateral offset, can change (e.g., from Extra Reduced, to Reduced, to Standard, to Extended, to Extra Extended) while a second geometric parameter, such as a leg length adjustment, can remain the same (such as always −8 mm along a particular row, for example). When moving along a particular column, e.g., from top to bottom along the tray, the second geometric parameter, e.g., the leg length adjustment, can change (e.g., from −8, to −4, to 0, to +4, to +8) while the first geometric parameter, e.g., the lateral offset, can remain the same (such as always being "Standard" along a particular column, for example). The layout of the tray allows a surgeon or other medical practitioner to quickly and easily select another provisional neck if the previous neck was unsatisfactory my moving along a row or column as appropriate to increase or decrease the lateral offset or the leg length.

In an example, controller 50 can be configured so that the view that is displayed to a user through user interface 54, such as on a touch screen user interface 54 as shown in FIG. 4, closely mimics, or is even substantially identical to, the physical appearance or layout of the physical tray that are also used by surgeons or other medical practitioners. For example, processor 56 can provide instructions to a display of user interface 54 to display a similar 5×5 two-dimensional array of "provisional necks" with the values of a first geometric parameter, e.g., lateral offset for a prosthetic hip, changing along the left-to-right axis of the array and a second geometric parameter, e.g., leg length for the prosthetic hip, changing along the top-to-bottom axis of the array. In such a configuration, the display of user interface 54, e.g., the touch screen, can provide a "virtual" provisional tray that closely mimics the physical appearance of a physical provisional tray that the surgeon or other medical practitioner is accustomed to, providing for ease of adoption with little or no additional training for the surgeon or other medical practitioner.

The ability to store a set of control mechanism output values or control signal values for any combination of geometric parameter values can also provide medical practitioners and prosthesis manufacturers with more flexibility in providing for patient care. Specifically, the ability to select and modify any geometric parameter allows a medical practitioner, such as a surgeon, to provide for better fine tuning of each geometric parameter without having to deal with and manage a large inventor of provisional components. In the example of hip prosthetics, the number of values for each geometric parameter that can be represented in a tray is practically limited by the number of physical provisional components that can be managed by the surgeon or other medical practitioner or her support staff during an operation. Thus, providing for changes of 1 millimeter for leg length adjustment in a physical provisional tray, rather than the 4 millimeters currently used by some systems (described above), while beneficial for patient care, can become too difficult for the surgeon or other medical practitioner to manage as it quadruples the number of provisional neck that need to be provided on a provisional hip tray. However, with a controller 50 having a set of control mechanism output values or control signal values for each possible combination of geometric parameters, no matter how many combinations there can be, the surgeon or other medical practitioner can be able to select 1 millimeter changes for leg length without additional confusion. A similar increase in the number of choices for other geometric parameters can also be provided to the surgeon or other medical practitioner.

Naturally, the increase in the number of choices for each geometric parameter can result in a corresponding increase in the number of permanent components that an implant manufacturer has to manufacture and that a medical practitioner or hospital has to stock. Therefore, there will be a natural tradeoff between the number of choices per geometric parameter and the number of different permanent components that a manufacturer can cost-effectively manufacture and that a medical practitioner can cost-effectively warehouse. However, the adjustable provisional component 20 and controller 50 of system 40 allows for considerably more flexibility and control in selecting the values of geometric parameters that can be provided for in an artificial prosthesis.

In an example, memory 58 and processor 56 can be programmed to calculate, on the fly, what a particular set of control mechanism output values or control signal values should be in order to provide for a set of geometric parameter values for adjustable provisional component 20 that are entered by a user. The calculations to determine control mechanism output values or control signal values can be determined based on the geometry of adjustable provisional component 20 and control mechanisms 30, e.g., physical size and shape of individual parts of adjustable provisional component 20. The ability to calculate output values or control signal values for each control mechanism 30 from an entered or selected set of geometric parameter values provides more flexibility for system 40 by allowing a user, such as a surgeon or other medical practitioner, to select from a much greater number of combinations when attempting to determine a good geometric fit.

Communication module 62 provides for communicating between processor 56 and control mechanisms 30. Communication module 62 can comprise a hardware-based communications device, such as a modem or other computing device that communicates with control mechanisms 30, e.g., through wires 52 or through a wired or wireless network, or communication module 62 can comprise a software-based communications protocol that allows processor 56 to communicate with control mechanisms 30. In an example, communication module 62 can be configured to receive instructions from processor 56 and convert the instructions into control signals that each correspond to a physical output value of a particular control mechanism 30. For example, an instruction from processor 56 could be converted by communication module 62 to an analog voltage value, wherein a physical position of a control mechanism 30 can correspond to the analog voltage value. In an example, the control signal communicated by communication module 62 can comprise a digital control signal that includes specific positional data that can be interpreted by a particular control mechanism 30. System 40 can comprise other intermediate communication devices, systems, or components that can generate, relay, amplify, or receive communication or control signals from controller 50 to control mechanism 30 of adjustable provisional component 20

Turning back to FIG. 4, system 40 can further comprise an output device, such as a printer 64 that is communicatively coupled to controller 50 via a communication link 66, such as a wired connection or through a network. After the surgeon or other medical practitioner has determined which values of one or more geometric parameter or parameters of interest will provide the best geometric fit for the patient, the output device identifies a corresponding permanent component, for example so that the user, e.g., a surgeon or other medical practitioner or a support staff member, can retrieve the corresponding permanent component. In an example, shown in FIG. 4, controller 50 can be configured to send to printer 64 a print out of identification information for a permanent component that corresponds to the desired provisional geometric parameters. The identification information can describe or identify a permanent implant that corresponds to the current or a previous geometric configuration of adjustable provisional component 20. For example, for the example system 40 shown in FIG. 4, wherein an adjustable provisional hip component 20 is being used, printer 64 can be configured to print out the manufacturer and any other identification information that is necessary to select the desired permanent implant. In the example shown in FIG. 4, printer 64 prints the manufacturer (Zimmer) and information that identifies a specific model and geometric configuration ("K9 Ext+4") that the user can refer to when retrieving a corresponding permanent hip implant from storage. An output device, such as printer 64, also can allow the user, e.g., a surgeon or other medical practitioner, to confirm that the identification information is consistent with the desired permanent component before submitting the information to support staff, such as supply personnel, to retrieve the permanent component from storage. The output device can also provide an additional level of confirmation that can be double checked by the user, e.g., a surgeon or other medical practitioner, when the permanent component is retrieved, e.g., by comparing the retrieved permanent component to the identification information from the output device to ensure there is a match.

The output device of system 40 need not be a printer 64, but can be any device or system that allows for communication of the identification information of the corresponding permanent component. Examples of other output devices include a device for sending a message, such as an electronic mail message, text message, or internal network message, from controller 50 to another computing device, such as a computer monitored by a member the supply department or a supply system, a display screen that is viewable by the user, e.g., a surgeon or other medical practitioner or support staff, an audio output device such as a speaker to play an audible sound that can be heard by a user, and the like.

In an example, controller 50 can be communicatively coupled to a supply-chain management system (not shown) to provide for an automatic indication of the use of a specific permanent component so that replacement of a permanent component can be automated. Automatic communication of the use of a permanent component can provide for reliable supply chain management by reducing the likelihood of human error associated with manually entering the specific permanent component into the supply-chain management system.

Turning back to FIG. 3, in an example, adjustable provisional component 20 can comprise one or more sensors 70A, 70B, 70C, 70D (collectively referred to herein as "sensor 70" or "sensors 70") that provide positional feedback of the geometric configuration of adjustable provisional component 20. Sensors 70 can be communicatively coupled to controller 50, such as through wires 52 or some other communication link, to provide updates of at least one of orientation of each sensor 70, a position of each sensor 79, a relative orientation of one sensor 70 with respect to one or more of the other sensors 70, or a relative position of one sensor 70 with respect to one or more of the other sensors 70. Each sensor 70 can be coupled to a specific component of adjustable provisional component 20 in order to provide for an orientation or positional measurement.

In an example, a first sensor 70A can be coupled to provisional head 24 and can provide an orientation measurement of provisional head 24, for example a biaxial orientation measurement, such as via an accelerometer or a gyroscopic orientation sensor, that can sense an orientation of provisional head 24 along at least two axes, e.g. along first axis 36 and second axis 38. A triaxial orientation sensor, such as a triaxial accelerometer or gyroscopic orientation sensor, can also be used. Sensors 70B and 70C can each be coupled to a specific section of provisional neck 22 and can provide for an orientation or positional measurement of a section of provisional neck 22 to which it is coupled, e.g., using a uniaxial, biaxial, or triaxial orientation sensor such as an accelerometer or a gyroscopic orientation sensor. A sensor 70D can also be coupled with an axial terminus of adjustable provisional component 20, such as on connector 26, in order to provide a positional measurement of the terminus, e.g., to determine an axial length of adjustable provisional component 20, wherein sensor 70D can determine its distance from a reference point, such relative to another sensor 70. Sensor 70D, or another sensor coupled to connector 26, can also provide for an orientation measurement of connector 26, such as with a biaxial or triaxial accelerometer or gyroscopic orientation sensor.

Examples of sensors that can be used to determine orientation include, but are not limited to, one or more tilt sensors, such as an inclinometer, a clinometer, a tilt meter, a tilt indicator, a gradient meter, a level gauge, an accelerometer, and a gyroscopic orientation sensor. Each sensor 70 can comprise a single sensor capable of performing the desired measurement, such as a biaxial or triaxial accelerometer, or can comprise a plurality of sensors that can be linked together to collectively provide for the desired measurement, such as a set of two uniaxial tilt sensors coupled together in a generally orthogonal arrangement to provide for biaxial sensing, a set of three uniaxial tilt sensors coupled together in a generally orthogonal arrangement to provide for triaxial sensing, or a single biaxial sensor and a single uniaxial sensor to provide for triaxial sensing.

Examples of sensors that can be used to determine position include, but are not limited to, one or more position sensors, such as at least one potentiometer, such as at least one string potentiometer at least one linear variable differential transformer, at least one rotary variable differential transformer, at least one hall effect sensor, at least one optical proximity sensor, at least one piezoelectric sensor, and at least one photodiode array. Each sensor 70, when used to measure position, can comprise one positional sensor, or a plurality of positional sensors, either of the same type or a different type, to determine the position of the sensor 70 in space or relative to a reference position.

Each sensor 70 can be communicatively linked to at least one other sensor 70 to provide for relative orientation or positional measurement of one part of adjustable provisional component 20 with respect to another part. For example, sensor 70A can be linked to sensor 70D to provide for an axial length measurement between sensors 70A and 70D in order to analyze the leg length change of adjustable provisional hip component 20. Sensor 70A can also be linked to sensor 70D to determine a relative orientation or a relative position of provisional head 24 with respect to connector 26, which in turn can provide for a determination of a relative orientation or a relative position of provisional head 24 with respect to the patient's femur. Similarly, each sensor 70B, 70C of provisional neck 22 can be linked to either sensor 70A or 70D to determine a relative orientation or a relative position of each part of provisional neck 22 with respect to provisional head 24 or connector 26, respectively.

Sensors 70 can be configured to provide feedback to controller 50 to determine whether desired values of the geometric parameters of interest are actually being achieved by control mechanisms 30. After repeated use, adjustable provisional component 20 may not respond exactly as initially thought to control mechanisms 30 such that a desired value of, for example, leg length or later offset may not be achieved. Sensors 70 allow controller 50 to determine whether the desired values of geometric parameters are reached, and if not, to indicate that corrective action be performed. A corrective action can comprise processor 54 calculating a correction factor for the output of one or more control mechanisms 30, processor 54 initiating an alarm indicating that the particular adjustable provisional component 20 is not responding properly, recalibrating the particular adjustable provisional component 20, or retiring the particular adjustable provisional component 20 from use.

Adjustable provisional component 20 and system 40 provides for several advantages over systems using a plurality of individual components each having a different geometric configuration. System 40 and adjustable provisional component 20 provide for provisional fitting of an implantable component, such as an implantable prosthetic, for example an artificial hip implant, with a single insertion and removal of adjustable provisional component 20, compared to multiple insertions and removals of provisional components when a component must be switched out in order to change the geometry. For the case of total hip replacement surgery, it is not uncommon for a surgeon or other medical practitioner to require four, five, six, or more provisional necks before an acceptable geometric fit is discovered, requiring the surgeon or other medical practitioner to perform four, five, six, or more insertions and removals of the provisional hip component before an adequate fit is achieved. The single insertion and removal of adjustable provisional component 20 provides for faster surgery times because the geometric configuration of adjustable provisional component 20 can be adjusted much more rapidly than can be done with non-adjustable provisional components. The single insertion and removal can also allow for a reduced chance of infection because it involves fewer external components being introduced into the patient during surgery.

The use of system 40 and single adjustable provisional component 20 rather than a plurality of non-adjustable provisional components also have several cost-savings and efficiency benefits. For example, the use of a single adjustable provisional component 20 rather than a tray comprising a plurality of individual pieces, such as twenty or more provisional components, can allow for a more cost-effective preparation process because there are fewer components to sterilize in order to prepare adjustable provisional component 20 for surgery. Moreover, there is less training required for support staff since there is only a single component to be prepared for surgery rather than a tray of twenty or more components which must be properly labeled, and properly placed and arranged in a tray, for example. The use of system 40 can also provide for reduced errors when retrieving a permanent component that corresponds to the desired geometry of adjustable provisional component 20 because system 40 can comprise an output device, such as printer 64, that allows for confirmation of the correct permanent implant by the surgeon or medical practitioner and an easy-to-use and easy-to-understand method of informing support staff, such as supply personnel, of the desired permanent component. System 40 can also provide for automatic notification to a supply-chain management system of the use of a particular permanent component in order to facilitate replacement of the permanent component in inventory.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed:

1. An adjustable provisional component for an implantable medical device, the adjustable provisional component comprising:
   a first portion comprising a neck and configured to be mountable to a first part of a patient comprising a stem;
   a second portion comprising a head coupled to the first portion; and
   a control mechanism comprising at least one of a servo motor and a jack screw;
   wherein at least one of the first portion and the second portion is adjustable by the control mechanism to select a value of a first geometric parameter of the adjustable provisional component; and
   wherein the first geometric parameter comprises a first one of the following geometries: a total length of the adjustable provisional component defined by the first and second portions, an angular orientation between the first and second portions, and a lateral offset between the first and second portions.

2. The adjustable provisional component of claim 1, wherein the at least one of the first portion and the second portion is further adjustable to select a value of a second geometric parameter of the adjustable component.

3. The adjustable provisional component of claim 2, wherein the second geometric parameter comprises a second one of the geometries.

4. The adjustable provisional component of claim 2, further comprising a second control mechanism for adjusting the at least one of the first portion and the second portion to adjust the second geometric parameter.

5. The adjustable provisional component of claim 4, wherein the second control mechanism comprises at least one of a servo motor and a jack screw.

6. A system comprising:
   an adjustable provisional component comprising:
      a first portion mountable to a first part of a patient, the first portion comprising a neck; and
      a second portion coupled to the first portion, the second portion comprising a head;
      wherein at least one of the first portion and the second portion is adjustable to select a value of a first geometric parameter of the adjustable provisional component;
   a control mechanism for adjusting the at least one of the first portion and the second portion to adjust the first geometric parameter, wherein the control mechanism comprises at least one of a servo motor and a jack screw; and
   a controlling computer configured to control the control mechanism;
   wherein the first geometric parameter comprises a first one of the following geometries: a total length of the adjustable provisional component defined by the first and second portions, an angular orientation between the first and second portions, and a lateral offset between the first and second portions.

7. The system of claim 6, comprising an output device to provide identification information of at least one of a selected value of the first geometric parameter of the adjustable provisional component and a permanent component corresponding to the selected value of the first geometric parameter.

8. The system of claim 6, wherein the at least one of the first portion and the second portion is further adjustable to select a value of a second geometric parameter of the adjustable component.

9. The system of claim 8, wherein the second geometric parameter comprises a second one of the geometries.

10. The system of claim 8, further comprising a second control mechanism for adjusting the at least one of the first portion and the second portion to adjust the second geometric parameter.

11. The system of claim 10, wherein the control computer is further configured to control the second control mechanism.

12. The system of claim 10, wherein the second control mechanism comprises at least one of a servo motor and a jack screw.

13. The system of claim 8, comprising an output device to provide identification information of at least one of a selected value of the first geometric parameter of the adjustable provisional component, a selected value of the second geometric parameter of the adjustable provisional component, and a permanent component corresponding to the selected value of the first geometric parameter and the selected value of the second geometric parameter.

14. An adjustable orthopedic provisional component comprising:
    an adjustable neck mountable to a stem of an artificial hip implant;
    a head mountable to the adjustable neck;
    wherein the neck is adjustable to select a value of one of a leg length adjustment, a value of a lateral offset between the head and the stem, or a version angle; and
    a control mechanism for adjusting the neck to adjust the one of the leg length adjustment, the lateral offset between the head and the stem, or the version angle;
    wherein the control mechanism comprises at least one of a servo motor and a jack screw.

15. The adjustable orthopedic provisional component of claim 14, wherein the neck is further adjustable to select a value of a second one of the leg length adjustment, the lateral offset between the head and the stem, and the version angle.

16. The adjustable orthopedic provisional component of claim 15, wherein the first geometric parameter comprises a first one of leg length, lateral offset between the head and the stem, and a version angle and the second geometric parameter comprises a second one of leg length, lateral offset between the head and the seam, and a version angle.

17. The adjustable orthopedic provisional component of claim 15, comprising a second control mechanism for adjusting the second one of the leg length adjustment, the lateral offset between the head and the stem, and the version angle.

18. The adjustable orthopedic provisional component of claim 17, wherein the second control mechanism comprises at least one of a servo motor and a jack screw.

* * * * *

UNITED STATES PATENT AND TRADEMARK OFFICE
CERTIFICATE OF CORRECTION

| | | |
|---|---|---|
| PATENT NO. | : 9,216,086 B2 | Page 1 of 1 |
| APPLICATION NO. | : 13/746618 | |
| DATED | : December 22, 2015 | |
| INVENTOR(S) | : Paul J. Conrad | |

It is certified that error appears in the above-identified patent and that said Letters Patent is hereby corrected as shown below:

In the claims,

In column 16, line 23, in Claim 16, delete "seam," and insert --stem,--, therefor Signed and Sealed this
Twenty-sixth Day of April, 2016

Michelle K. Lee
*Director of the United States Patent and Trademark Office*